(12) United States Patent
Bushfield et al.

(10) Patent No.: US 10,465,186 B2
(45) Date of Patent: Nov. 5, 2019

(54) ANTIBODY IDENTIFICATION BY LINEAGE ANALYSIS

(71) Applicant: Epitomics, Inc., Cambridge (GB)

(72) Inventors: Mark Bushfield, Cambridge (GB); Michael Hadjisavas, Foster City, CA (US); Luc Adam, Hayward, CA (US)

(73) Assignee: EPITOMICS, INC., Burlingame, CA (US)

( * ) Notice: Subject to any disclaimer, the term of this patent is extended or adjusted under 35 U.S.C. 154(b) by 677 days.

(21) Appl. No.: 14/911,436

(22) PCT Filed: Aug. 13, 2014

(86) PCT No.: PCT/US2014/050945
§ 371 (c)(1),
(2) Date: Feb. 10, 2016

(87) PCT Pub. No.: WO2015/026606
PCT Pub. Date: Feb. 26, 2015

(65) Prior Publication Data
US 2016/0319275 A1   Nov. 3, 2016

Related U.S. Application Data

(60) Provisional application No. 61/867,371, filed on Aug. 19, 2013.

(51) Int. Cl.
| | |
|---|---|
| *A61K 38/00* | (2006.01) |
| *G01N 33/53* | (2006.01) |
| *C12N 15/10* | (2006.01) |
| *G16B 30/00* | (2019.01) |
| *G16B 35/00* | (2019.01) |
| *G16C 20/60* | (2019.01) |
| *C07K 16/00* | (2006.01) |
| *G01N 33/68* | (2006.01) |
| *C07K 16/32* | (2006.01) |
| *C07K 16/46* | (2006.01) |
| *C12P 21/00* | (2006.01) |

(52) U.S. Cl.
CPC .......... *C12N 15/1089* (2013.01); *C07K 16/00* (2013.01); *C07K 16/32* (2013.01); *C07K 16/46* (2013.01); *C12P 21/005* (2013.01); *G01N 33/6854* (2013.01); *G16B 30/00* (2019.02); *G16B 35/00* (2019.02); *G16C 20/60* (2019.02); *C07K 2317/10* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 2006/0099204 A1 | 5/2006 | Couto |
| 2010/0204059 A1 | 8/2010 | Ke et al. |
| 2010/0317539 A1 | 12/2010 | Yu |
| 2011/0065112 A1* | 3/2011 | Yu .............................. C12Q 1/68 435/6 |

OTHER PUBLICATIONS

Wu (Science. Sep. 2011:;33(6049):1593-1602). (Year: 2011).*
Reddy, et al. "Monoclonal antibodies isolated without screening by analyzing the variable-gene repertoire of plasma cells", Nat Biotechnol. Sep. 2010;28(9):965-9.
Wu, et al, "Focused evolution of HIV-1 neutralizing antibodies revealed by structures and deep sequencing", Science. Sep. 16, 2011;333(6049):1593-602.

* cited by examiner

*Primary Examiner* — Michail A Belyavskyi
(74) *Attorney, Agent, or Firm* — James S. Keddie; Bozicevic, Field & Francis LLP

(57) ABSTRACT

A method of screening is provided. In certain embodiments, the method involves a) obtaining the nucleotide sequences of: i. a heavy chain-encoding nucleic acid that encodes the variable domain of a heavy chain of a first antibody of an animal; and ii. a light chain-encoding nucleic acid that encodes the variable domain of a light chain of the first antibody; b) obtaining nucleotide sequences of cDNAs encoding at least a portion of the antibody repertoire of the animal; c) computationally screening the sequences obtained in b) to identify heavy and light chain sequences that are related by lineage to the heavy and light chain sequences of a); and d) testing at least one pair of the heavy and light chain sequences identified in c) to identify a second antibody that binds to the same antigen as the first antibody.

15 Claims, 1 Drawing Sheet

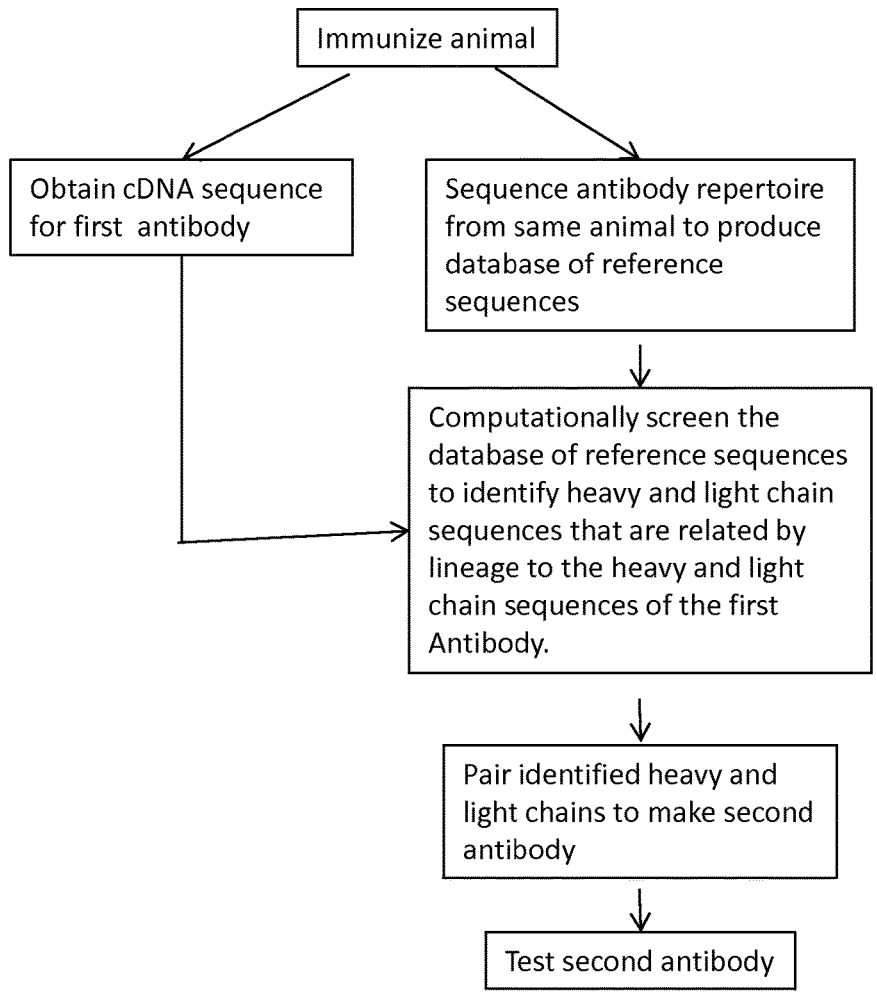

ANTIBODY IDENTIFICATION BY LINEAGE ANALYSIS

FIELD OF THE INVENTION

The invention relates to monoclonal antibodies.

BACKGROUND TO THE INVENTION

Antibodies are proteins that bind a specific antigen. Generally, antibodies are specific for their targets, have the ability to mediate immune effector mechanisms, and have a long half-life in serum. Such properties make antibodies powerful therapeutics. Monoclonal antibodies are used therapeutically for the treatment of a variety of conditions including cancer, inflammation, and other diseases. There are currently over two dozen therapeutic antibody products on the market and hundreds in development. There is a constant need for new antibodies having desirable properties and methods for isolating the same.

It is understood that an the full antibody repertoire of an immunized subject (also referred as "immunized antibody repertoire" or "immunized repertoire") contains a very large number of antibodies having sequence diversity which can, in some cases, impart variations with respect to affinity, specificity and in vivo functionality. In view of this it is sometimes desirable to sample a significant number of antibodies from a subject to identify antibodies that possess similar or improved properties relative to, e.g., an antibody of interest. Therefore there is a need in the art for the identification of new antibodies in a direct and efficient manner for use in the development of therapeutic candidates, in diagnostic applications and/or research products.

US20110065112 describes a method for identifying lineage-related antibodies. In some embodiments this method involves: obtaining the antibody sequences from a population of B cells; grouping the antibody sequences to provide a plurality of groups of lineage-related antibodies; testing a single antibody from each of the groups in a bioassay and, after the first antibody has been identified, testing further antibodies that are in the same group as the first antibody in a second bioassay. US20110065112 also describes a method that involves testing a plurality of antibodies obtained from a first portion of an antibody producing organ of an animal; obtaining the sequence of a first identified antibody; obtaining from a second portion of said antibody producing organ the sequences of further antibodies that are related by lineage to said first antibody; and, c) testing the further antibodies in a second bioassay.

US20100204059 describes a method for obtaining nucleic acid encoding a plurality of antibodies. In certain embodiments, the method comprises obtaining from an immunized animal nucleic acid encoding the amino acid sequence of the heavy and light chains of a second antibody that binds to the antigen as a first antibody and differs in amino acid sequence to the first antibody, wherein the obtaining is done by amplification using: i. a first primer pair that includes oligonucleotides are complementary to CDR-encoding regions first antibody.

The inventors have developed a new method that serves to identify lineage-related antibodies from an antibody repertoire of an immunized animal, based on the properties of an antibody of interest using computational means.

SUMMARY OF THE INVENTION

According to a first aspect of the invention a method of screening is provided. In certain embodiments, the method involves a) obtaining the nucleotide sequences of: i. a heavy chain-encoding nucleic acid that encodes the variable domain of a heavy chain of a first antibody of an animal; and ii. a light chain-encoding nucleic acid that encodes the variable domain of a light chain of the first antibody;
b) obtaining nucleotide sequences of cDNAs encoding at least a portion of the antibody repertoire of the animal;
c) computationally screening the sequences obtained in b) to identify heavy and light chain sequences that are related by lineage to the heavy and light chain sequences of a); and d) testing at least one pair of the heavy and light chain sequences identified in c) to identify a second antibody that binds to the same antigen as the first antibody.

According to a further aspect of the invention there is provided a method of producing an antibody, the method comprising a) obtaining the nucleotide sequences of: i. a heavy chain-encoding nucleic acid that encodes the variable domain of a heavy chain of a first antibody of an animal; and ii. a light chain-encoding nucleic acid that encodes the variable domain of a light chain of the first antibody;
b) obtaining nucleotide sequences of cDNAs encoding at least a portion of the antibody repertoire of the animal;
c) computationally screening the sequences obtained in b) to identify heavy and light chain sequences that are related by lineage to the heavy and light chain sequences of a);
d) introducing at least one pair of the heavy and light chain sequences obtained in c) into a host cell;
e) incubating the host cell to permit expression of the antibody;
f) purifying the antibody expressed in e) to produce a second antibody that binds to the same antigen as the first antibody.

BRIEF DESCRIPTION OF THE DRAWINGS

FIG. 1 is a flow diagram illustrating one embodiment of the invention.

DEFINITIONS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions (VL and VH respectively) are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa, or about 200 to 225 amino acids, or about 214 amino acids) comprise a variable region of about 110 amino acids at the $NH_2$-terminus and a kappa or lambda constant region at the COOH-terminus. Full-length immunoglobulin "heavy chains" (of about 50 kDa, or about 440 to 460 amino acids), or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, $F(ab')_2$, and or other antibody fragments that retain specific binding to antigen, and monoclonal antibodies.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response (or non-immunogenic) in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a capture agent (antibody) and analyte when they are specifically bound in a capture agent/analyte complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$ M, or less than about $10^{-12}$ M.

A "variable region" of a heavy or light antibody chain is an N-terminal mature domain of the chains. All domains, CDRs and residue numbers are assigned on the basis of sequence alignments and structural knowledge. Identification and numbering of framework and CDR residues is as described in by Kabat, Chothia (Chothia Structural determinants in the sequences of immunoglobulin variable domain. J Mol Biol 1998; 278:457-79) or others.

VH is the variable domain of an antibody heavy chain. VL is the variable domain of an antibody light chain, which could be of the kappa (K) or of the lambda isotype. K-1 antibodies have the kappa-1 isotype whereas K-2 antibodies have the kappa-2 isotype.

A "buried residue" is an amino acid residue whose side chain has less than 50% relative solvent accessibility, which is calculated as the percentage of the solvent accessibility relative to that of the same residue, X, placed in an extended GGXGG peptide. Methods for calculating solvent accessibility are well known in the art (Connolly 1983 J. appl. Crystallogr, 16, 548-558).

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

The terms "treatment", "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

"Corresponding amino acids", as will be described in greater detail below, are amino acid residues that are at an identical position (i.e., they lie across from each other) when two or more amino acid sequences are aligned. Methods for aligning and numbering antibody sequences are set forth in great detail in Chothia, supra, Kabat supra, and others. As is known in the art (see, e.g. Kabat 1991 Sequences of Proteins of Immunological Interest, DHHS, Washington D.C.), sometimes one, two or three gaps and/or insertions of up to one, two, three or four residues, or up to about 15 residues (particularly in the L3 and H3 CDRs) may be made to one or both of the amino acids of an antibody in order to accomplish an alignment.

A "natural" antibody is an antibody in which the heavy and light immunoglobulins of the antibody have been naturally selected and paired by the immune system of a multicellular organism, as opposed to unnaturally paired antibodies made by e.g. phage display. As such, the subject parental antibodies do not usually contain any viral (e.g., bacteriophage M13)-derived sequences. Spleen, lymph nodes and bone marrow are examples of tissues that produce natural antibodies. For example, the antibodies produced by the antibody producing cells isolated from an animal immunized with an antigen are natural antibodies.

The term "non-naturally paired", with respect to VH and VL chains of an engineered antibody, refers to an antibody that contains a naturally occurring VH sequence and a naturally occurring VL sequence, where the sequences are not paired with one another naturally, i.e., in a natural antibody. Thus, a non-naturally paired antibody is a combination of VH and VL chain of two different natural antibodies. The VH and VL chains of a non-naturally paired antibody are not mutated relative to the VH and VL chains of the two different antibodies which provided the VH and VL chains. For example, the "non-naturally paired" IgH and IgL chains of the engineered antibody may contain the IgH variable chain from a first antibody producing cell obtained from an animal and the IgL variable chain of second antibody producing cell obtained from the same animal, where the amino acid sequence of the antibody produced by the first cell is different from the amino acid sequence of the antibody produced by the second cell. In this example, the IgH and IgL chains may be from the same lineage group. An antibody containing "non-naturally paired" IgH and IgL chains may or may not be made by phage display. As such, antibodies may or may not contain viral (e.g., bacteriophage M13)-derived sequences.

The term "lineage-related antibodies" and "antibodies that are related by lineage" as well as grammatically-equivalent variants thereof, are antibodies that are produced by cells that share a common B cell ancestor or convergence toward similar sequence during affinity maturation. Related antibodies produced by related antibody producing cells bind to the same epitope of an antigen and are typically very similar in sequence, particularly in their L3 (i.e., the light chain CDR3) and H3 (heavy chain CDR3) regions. Both the H3 and L3 CDRs of antibodies that are related to one another by lineage have an identical length and a near identical sequence (i.e., differ by up to 5, i.e., 0, 1, 2, 3, 4 or 5 residues). The VH or VL domains of antibodies within a related group of antibodies may have amino acid sequences that are at least about 80% identical (e.g., at least 85% identical, at least 90% identical, at least 95% or at least 98% or at least 99% identical), ignoring any gaps or insertions made to facilitate alignment of the sequences. In certain cases, the B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies are related via a common antibody ancestor, e.g., the antibody produced in the naïve B cell ancestor. The term "related antibodies" is intended to describe a group of antibodies that are produced by cells that arise from the same ancestor B-cell. A "lineage group" contains a group of antibodies that are related to one another by lineage.

DETAILED DESCRIPTION OF THE INVENTION

One embodiment of the subject method is illustrated in FIG. 1. With reference to FIG. 1, the method may involve obtaining the cDNA sequences for a first antibody from an animal. As would be apparent, this step involves obtaining the nucleotide sequences of: i. a VH cDNA, wherein the VH cDNA encodes the variable domain of a heavy chain of the first antibody; and ii. a VL cDNA, wherein the VL cDNA encodes the variable domain of a light chain of the first antibody. In addition, the method involves obtaining the nucleotide sequences of cDNAs, i.e., heavy and light chain cDNAs, encoding at least a portion of the antibody repertoire of the same animal (i.e., the same individual) to produce reference sequences. These cDNAs may be obtained in bulk preparation from mRNA prepared from a population of antibody-producing cells, e.g., spleen or plasma cells, isolated from the animal. In many cases, the sequences obtained in this step may be deposited into a database, and optionally annotated as to whether they are heavy chain or light chain sequences. In the next step, the reference sequences, i.e., the sequences obtained by sequencing the repertoire of the animal, are screened computationally to identify heavy and light chain sequences that are related by lineage to the heavy and light chain sequences of the first antibody. Such antibodies generally have very similar sequences, and have H3 CDRs of identical length and near identical sequence as well as L3 CDRs of identical length and a near identical sequence. This step may be done by comparing a window (e.g., at least 20, 30, 50, 80 or 100 contiguous amino acids) of the heavy and light chain of the first antibody with the reference sequences to identify similar sequences. Alternatively, this step may be done by scanning the reference sequences to identify those that encode sequences that are similar or identical to the heavy chain CDR3 and light chain CDR3 sequences of the first antibody. In this embodiment, the initial steps of this part of the method may be done by comparing only the heavy and light chain CDR3 sequences of the first antibody to the reference sequences. This step may result in a list of heavy chain sequences and a list of light chain sequences, where the heavy chain sequences on the list are from heavy chains of antibodies that are related by lineage to the heavy chain of the first antibody and the light chain sequences on the list are from light chains of antibodies that are related by lineage to the light chain of the first antibody. Depending on how the library preparation and sequencing is done, the heavy and light chain sequences may already be paired in the sense that when a heavy chain sequence is identified, the light chain to which that heavy chain is naturally paired may be apparent. In other embodiments, there may be no information about how the heavy and light chains are naturally paired. Once the list of heavy chain sequences and the list of light chain sequences have been created, the method involves testing at least one pair of the heavy and light chain sequences to identify a second antibody that binds to the same antigen as the first antibody. In some cases, this may involve amplifying cDNA sequences encoding the heavy and light chains by PCR from a pool of cDNA (e.g., the same pool of cDNA that was sequenced earlier in the method) and expressing the amplified cDNAs in a cell. In other embodiments, the heavy and light chain sequences can be made synthetically and expressed in a cell. In some embodiments, the testing step may comprises testing at least 10% of all possible combinations of the identified heavy and light chains for binding to the antigen. In particular embodiments, the heavy and light chain sequences tested may be randomly selected from the identified heavy and light chain sequences.

The present method provides a way to efficiently screen millions or tens of millions of antibody sequences without having to screen each of the antibodies individually as is done in conventional methods. The method allows one to home in on a group of heavy chain sequences and a group of light chain sequences, the individual sequences of which can be tested in a pairwise manner and, optionally, mutated (e.g., using the methods set out in US20050033031) with the knowledge that most or all of the candidate antibodies are capable of binding to the target antigen. The candidate antibodies are expected to vary in their biochemical and/or pharmacological properties (e.g., they may vary in their affinity, specificity and/or in vivo functionality, etc.). As such, after they have been produced, the candidate antibodies can be tested for a desirable property.

Some embodiments of the present method allow one to harness and make use of the diversity of sequences in an antibody repertoire in a way that is inaccessible by other methods.

For example, methods in which phylogenetically-related antibodies are identified by PCR using primers to the CDR regions can be limited because, in some cases, the primers actually overwrite the sequences that provide antibody diversity. For example, if a CDR3 primer is used, any sequence mismatches in the CDR3 region will be overwritten by the primer, resulting in a PCR product that does not actually reflect the diversity of the original antibody population. The resultant PCR product may encode a functional antibody but the sequences variations at the primer binding site may have been overwritten. In other words, the primers used in several PCR-based methods are specifically designed to bind to sequence that are modified during affinity maturation. Use of such primers will frequently not result in a PCR product that reflects the original sequence.

Further, in some cases, PCR-based methods can only, at best, amplify a fragment encoding only part of a heavy or light chain (e.g., sequences that are 5' or 3' to one of the primers) rather than, for example, the entire variable domain of a heavy or light chain. While one can potentially piece together the two ends of a heavy or light chain coding sequence to produce a functional sequence (e.g., by performing another round of PCR to obtain an overlapping fragment and then joining the fragments together) this additional step adds significant technical complexity to the method and, because the initial PCR reactions are done on a pool of sequences, the 5' end of the heavy or light chain from one antibody can become be fused with a 3' end sequence from another antibody.

Finally, the sequence comparison algorithms used in the present method can be tuned to identify phylogenetically distant family members (e.g., family members that have, e.g., CDR3 regions with more than 3, 4, or 5 amino acid substitutions relative to the test sequence) that may not be amplified using PCR-based strategies. In these methods, the sequence comparison step could use an algorithm that identifies approximate patterns rather than exact patterns (e.g., a fuzzy match algorithm or the like) to identify sequences that have CDR sequences that are significantly different from the reference sequence. In contrast, CDR-based PCR may narrow the analysis down for example by introducing a bias meaning more distant family members will be missed as a consequence. This method may be particularly informative should gene conversion shift antigen reactivity away from the reference sequence to another lineage.

Many warm-blooded animals, in particular mammals such as humans, rabbits, mice, rats, sheep, cows, pigs, goats, horse, camel and ayes such as chickens and turkeys, may be used as a source of antibody-producing cells. However, in certain embodiments a rabbit or mouse is used because of their ease in handling, well-defined genetic traits, and the fact that they may be readily sacrificed. Procedures for immunizing animals are well known in the art, and are described in Harlow et al., (*Antibodies: A Laboratory Manual*, First Edition (1988) Cold Spring Harbor, N.Y.). In some embodiments the antibody repertoire of the animal may be obtained by sequencing cDNAs encoding heavy and light chains made from splenocytes of the animal. In other embodiments, the method may involve sequencing cDNAs encoding heavy and light chains made from circulating B cells of the animal.

In some embodiments, the animal may be been immunized with the antigen, e.g., multiple times in the presence of an adjuvant. In these embodiments, suitable antigens include extracellularly-exposed fragments of Her2, GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL-related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (co-stimulator for CD28 and CTLA-4), complement component C5, CTLA, EGFR, eotaxin (cytokine A11), HER2/neu, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFβR (Beta platelet-derived growth factor receptor), PMSA, renal carcinoma antigen G250, RSV, E-Selectin, TGFbeta1, TGFbeta2, TNFalpha, TRAIL-R1, VAP-1 (vascular adhesion protein 1), TNFα, or the like. In many embodiments, a peptide having the amino acid sequence corresponding to a portion of an extracellular domain of one of the above-listed proteins may be employed as an antigen.

In other embodiments, the animal may have an autoimmune disease, or has developed resistance to or has recovered from a disease (e.g., cancer). In some embodiments, antibody-producing cells may also be obtained from a subject that has generated the cells during the course of a selected disease or condition. For instance, antibody-producing cells from a human with a disease of unknown cause, such as rheumatoid arthritis, may be obtained and used in an effort to identify antibodies which have an effect on the disease process or which may lead to identification of an etiological agent or body component that is involved in the cause of the disease. Similarly, antibody-producing cells may be obtained from subjects with disease due to known etiological agents such as malaria or AIDS. These antibody-producing cells may be derived from the blood, lymph nodes or bone marrow, as well as from other diseased or normal tissues. Antibody producing cells may also be prepared from blood collected with an anticoagulant such as heparin or EDTA. The antibody-producing cells may be further separated from erythrocytes and polymorphs using standard procedures such as centrifugation with Ficoll-Hypaque (Pharmacia, Uppsula, Sweden). Antibody-producing cells may also be prepared from solid tissues such as lymph nodes or tumors by dissociation with enzymes such as collagenase and trypsin in the presence of EDTA.

The cDNAs encoding the first antibody may be obtained by any suitable means. In particular embodiments, the first antibody may be obtained by conventional hybridoma technology. In other embodiments, however, the method may employ flow cytometry (FACS) of cell populations obtained from rabbit spleen, bone marrow, lymph node, plasma or other lymph organs, e.g., through incubating the cells with labeled antigen and sorting the labeled cells using a cell sorter. The first antibody may also be identified by B cell cloning, i.e., screening individual B cells for an antibody of interest, and then amplifying the coding sequences of that antibody from the B cell from which the antibody is secreted, before the B cells dies and/or the mRNA encoding the antibody becomes degraded. A number of methods can be used to identify an antibody of interest, and clone its cDNA. In an exemplary embodiment, nucleic acids encoding the VH and VL domains of an antibody are isolated from an antibody-producing cell, e.g., a hybridoma. In order to produce antibody-producing hybridoma, an animal can be immunized with an antigen and once a specific immune response of the rabbit has been established, cells from the spleen of the immunized animal are fused with a suitable immortal cell (e.g., NIH 3T3, DT-40 or 240E cell, etc.; Spieker-Polet et al, Proc. Natl. Acad. Sci. 92: 9348-9352, 1995) to produce hybridoma cells. Supernatants from these hybridoma cells are screened for antibody secretion by enzyme-linked immunosorbent assay (ELISA) and positive clones secreting monoclonal antibodies specific for the antigen can be selected and expanded according to standard procedures (Harlow et al., *Antibodies: A Laboratory Manual*, First Edition (1988) Cold spring Harbor, N.Y.; and Spieker-Polet et al., supra).

In some embodiments, the antibody-producing cells may be obtained from the animal at a time when the transit of plasma cells in the blood is maximal. In some cases, this may be done shortly after (i.e., within 2 to 14 days of, e.g., 2-4, 3-5, 4-6, 5-7, 6-8, 7-9, 8-10, 9-11, 10-12, 11-13 or 12-14 days of) the initial immunization, the secondary immunization or a tertiary immunization. In any embodiment, the cells may be plated in a minimal amount of culture medium at a single cell dilution, maintained in culture for a period of time (e.g., 1-7 days) and culture medium may be tested for antibodies that react with the antigen before the plasma cells die. In any embodiment, the plated cells may be stimulated to produce more antibody while they are in culture. These embodiments do not require that the plasma cells divide in culture however, in some embodiments, the plasma cells may divide for a few generations. In these embodiments, the B cells can be separated from other cells by FACS prior to plating at single cell dilution.

As would be recognized, the cDNAs from the single cells may be barcoded so that they can be mixed together, optionally with other templates, and sequenced. In an exemplary embodiment, the heavy and light chain cDNAs are both barcoded with the same sequence, thereby allowing the sequences for those cDNAs to be paired with one another after the cDNAs have been mixed with other templates and sequenced.

In particular embodiments, the animal may be immunized by multiple antigens (e.g., at least 2, at least 5, at least 10, at least 50, at least 100, at least 500 or at least 1,000, up to 5,000 or more antigens).

Suitable monoclonal antibodies may be further selected on the basis of binding activity, including its binding specificity, binding affinity, binding avidity, a blocking activity or any other activity that causes an effect (e.g. promoting or inhibiting a cellular phenotype, e.g., cell growth, cell proliferation, cell migration, cell viability (e.g., apoptotis), cell differentiation, cell adherence, cell shape changes (e.g., tubular cell formation), complement dependent cytotoxicity CDC, antibody-dependent cell-mediated cytotoxicity ADCC, receptor activation, gene expression changes, changes in post-translational modification (e.g., phosphorylation), changes in protein targeting (e.g., NFκB localization etc.), etc., or inhibition of receptor multimerization (e.g., dimer or trimerization) or receptor-ligand interactions). In other embodiments, an affinity purification method maybe utilized to isolate antibody producing cells that produce antibodies that bind to an antigen. The antigen with which the animal was immunized may be immobilized on a solid phase and used to selectively retain antibody producing cells that express an antibody on their surface that binds to the antigen, while other cells are washed away. The retained cells may then be eluted by a variety of methods, such as by using an excess of the antigen, chaotropic agents, changing the pH, salt concentration, etc. Any of the well-known methods for immobilizing or coupling antigen to a solid phase may be used. For example, when the antigen is a cancer cell, appropriately treated microtiter plate that will bind to cells may be used, such as microtiter plates for cell culture. In the instances where the antigen is a protein, the protein may be covalently attached to a solid phase, for example, sepharose beads, by well-known techniques, etc. Alternatively, a labeled antigen may be used to specifically label cells that express an antibody that binds to the antigen and the labelled cells may then be isolated by cell sorting (e.g., by FACS). In certain cases, methods for antibody purification may be adapted to isolate antibody producing cells. Such methods are known and are described in, for example, J Immunol Methods. 2003 November; 282(1-2): 45-52; J Chromatogr A. 2007 Aug. 10; 1160(1-2):44-55; J Biochem Biophys Methods. 2002 May 31; 51 (3):217-31. Cells may also be isolated using magnetic beads or by any other affinity solid phase capture method, protocols for which are known. In some embodiments, antigen-specific antibody producing cells may be obtained from blood by flow cytometry using the methods described in Wrammert (Nature 2008 453: 667-672), Scheid (Nature 2009 458: 636-640), Tiller (J. Immunol. Methods 2008 329 112-124) or Scheid (Proc. Natl. Acad. Sci. 2008 105: 9727-9732), for example, which are incorporated by reference for disclosure of those methods. Exemplary antibody-producing cell enrichment methods include performing flow cytometry (FACS) of cell populations obtained from a spleen, bone marrow, lymph node or other lymph organs, e.g., through incubating the cells with labeled anti-rabbit IgG and sorting the labeled cells using a FACSVantage SE cell sorter (Becton-Dickinson, San Jose, Calif.). In some embodiments, single or nearly single antibody-producing cells are deposited in microtiter plates. If the FACS system is employed, sorted cells may be deposited after enrichment directly into a microtiter plate.

In some cases, the first antibody may have been tested in a bioassay to show that it has a biological activity. The bioassay may determine whether the antibody has a biological effect, e.g., an ability to inhibit an interaction between a receptor and an a ligand by either binding to the receptor and blocking binding of the ligand, or by binding to the ligand and neutralizing it, or by promoting or inhibiting a cellular phenotype, examples of which are described above. Such bioassays are well known in the art. Bioassays useful in this method are numerous, and include but are not limited to cellular assays in which a cellular phenotype is measured, e.g., gene expression assays; and in vivo assays that involve a particular animal (which, in certain embodiments may be an animal model for a condition related to the target).

The antibody repertoire of the animal may be sequenced by any suitable method. See, e.g., Reddy et al (Nat. Biotechnol. 2010 28:965-9), Fischer (MAbs. 2011 3:17-20) and Benichou et al (Immunology. 2012 135:183-91). Sequences encoding heavy and light chains may be amplified from the cDNA using techniques well known in the art, such as Polymerase Chain Reaction (PCR). See Mullis, U.S. Pat. No. 4,683,195; Mullis et al., U.S. Pat. No. 4,683,195; Polymerase Chain Reaction: Current Communication in Molecular Biology, Cold Springs Harbor Press, Cold Spring Harbor, N.Y., 1989. Briefly, cDNA segments encoding the variable domain of the antibody are exponentially amplified by performing sequential reactions with a DNA polymerase. The reaction is primed by a 5' primer and a 3' DNA primer. In some embodiments, the 3' antisense primer corresponding to a DNA sequence in the constant (or joining) region of the immunoglobulin chain and the 5' primer (or panel of related primers) corresponding to a DNA sequence in the variable region of the immunoglobulin chain or within the conserved leader sequence. This combination of oligonucleotide primers has been used in the PCR amplification of murine immunoglobulin cDNAs of unknown sequence (see Sastry et al., Proc Natl. Acad. Sci. 86:5728-5732, 1989 and Orlandi et al., Proc. Natl. Acad. Sci. 86:3833-3837, 1989). Alternatively, an "anchored polymerase chain reaction" may be performed (see Loh et al., Science 243:217-220, 1989). In this procedure, the first strand cDNA is primed with a 3' DNA primer as above, and a poly(dG tail) is then added to the 3' end of the strand with terminal deoxynucleotidyl transferase. The product is then amplified by PCR using the specific 3' DNA primer and another oligonucleotide consisting of a poly(dC) tail attached to a sequence with convenient restriction sites. In many embodiments, however, the entire polynucleotide encoding a heavy or light chain variable domain is amplified using primers spanning the first and last codons of those regions. In certain cases, universal primers may be used. Suitable restriction sites and other tails may be engineered into the amplification oligonucleotides to facilitate cloning and further processing of the amplification products. Amplification procedures using nested primers may also be used, where such nested primers are well known to one of skill in the art. Exemplary methods for amplifying antibody-encoding nucleic acid is also described in Wrammert (Nature 2008 453: 667-672) and Scheid (Nature 2009 458: 636-640), for example. Several strategies for cloning antibody sequences by PCR are known and may be readily adapted for use in the instant method (e.g., by using a CDR-specific primer in addition to a disclosed primer). Such strategies include those described by: LeBoeuf (Gene. 1989 82:371-7), Dattamajumdar (Immunogenetics. 1996 43:141-51), Kettleborough (Eur. J. Immunol. 1993 23:206-11), Babcook (A novel strategy for generating monoclonal antibodies from single, isolated lymphocytes producing antibodies of defined specificities Proc. Natl. Acad. Sci. 1996 93: 7843-7848) and Williams (Cold Spring Harb. Symp. Quant. Biol. 1989 54:637-47) as well as many others. In certain cases, the second primer may be a mixture of different primers or degenerate primers, for example.

In this embodiment, the antibody-producing cells may be combined before sequencing (in which case the initial amplification product will contain a mixture of a plurality of different products that can be discriminated by cloning the products or using single molecule sequencing technologies), or the cells may be kept separate from one another (in which case the initial amplification product amplified from a single cell may contain a single species that can be sequenced). In particular embodiments, particularly if the antigen elicits a strong response in the animal, the antibody repertoire may be sequenced in the absence of any antigen-based enrichment of antibody producing cells. In these embodiments, the method may involve: a) obtaining the antibody heavy chain sequences and the antibody light chain sequences from a population of B cells of an animal, wherein the population of B cells is not enriched for B cells that produce antibodies that specifically bind to a target antigen. In particular embodiments, this part of the method involves amplifying a population of nucleic acids that encode heavy and light chains by PCR from cDNA made from antibody-producing cells of the animal, and then sequencing the population of nucleic acids.

This step may comprise obtaining nucleotide sequences encoding at least 1% (e.g., at least 2%, at least 5% or at least 10%) of the antigen-reactive antibody repertoire of the animal. This may be accomplished by sequencing heavy and light chain cDNAs from 5,000, at least 10,000, at least 50,000, or at least 100,000, or more antibody producing cells.

In some embodiments, the reference heavy and light chain sequences may be deposited into a database without analysis. In other embodiments, the sequences may be analyzed, e.g., to determine whether they are heavy chain sequences or light chain sequences, etc.

In the next step, the sequence obtained from the first antibody is used to screen the reference sequences to identify antibodies that are related by lineage to the first antibody. The variable regions of antibodies within a related group of antibodies have amino acid sequences that are very similar. For example, the VH or VL domains of antibodies within a related group of antibodies may have amino acid sequences that are at least about 80% identical (e.g., at least 85% identical, at least 90% identical, at least 95% identical, at least 98% identical or at least 99% identical), ignoring any gaps or insertions made to facilitate alignment of the sequences. Antibodies within a related group of antibodies have VL domains that are similar to each other, as well as VH domains that are similar to each other. In other words, in certain embodiments the VH or VL domains of two different antibodies that are related to each other by lineage usually contain up to about ten (i.e., one, two, three, four or five or more) amino acid differences. An amino acid difference may be present at any position of the variable domain, including in any CDR or in any framework region. In these embodiments, any suitable sequence comparison program, e.g., BLAST (Altschul et al., *J. Mol. Biol.* 215:403-10, 1990) comparisons may be performed using default parameters, including choosing the BLOSUM62 matrix, an expect threshold of 10, low complexity filter off, gaps allowed, and a word size of 3. A sequence comparison may be done using DNA sequence or translated protein sequence. In some embodiments, the reference sequences may have been analyzed and placed into lineage groups (one set of groups for the heavy chains and another set of groups for the light chains, if the pairing is unknown) before the sequences are screened to identify heavy and light chains that are in the same lineage group as the heavy and light chains of the first antibody.

In some embodiments, the amino acid positions of the first antibody may be numbered using a suitable numbering system, such as that provided by Chothia (J Mol Biol 1998; 278: 457-79) or Kabat (1991, Sequences of Proteins of Immunological Interest, DHHS, Washington, D.C.). CDR and/or framework residues may be identified using these methods. Antibodies that are related to another by lineage also have H3 CDRs that are almost identical, as well as L3 CDRs that are almost identical. In these embodiments, any two antibodies that are related will have L3 and H3 CDRs that are each identical in length and have near identical sequences (i.e., that contain 0, 1, 2, 3, 4 or 5 amino acid changes). In other words the L3 CDRs of the two antibodies are identical in length and near identical in sequence and the H3 CDRs of the two antibodies are identical in length and near identical in sequence. In these embodiments, the reference sequences may be searched for a motif, e.g., the heavy and light chain CDR3 regions, using a motif searching algorithm.

Methods for identifying antibodies that are related by lineage are known and are described in a number of publications including Magori-Cohen (Bioinformatics 2006 22: e332-40), Manske (Clin. Immunol. 2006 120:106-20), Kleinstein (J. Immunol. 2003 171: 4639-49), Clement (Mol. Ecol. 2000 9: 1657-1659), Mehr (J. Immunol. 2004 172 4790-6), Wrammert (Nature 2008 453:667-672), Scheid (Nature 2009 458: 636-640), which are incorporated by reference herein for disclosure of those methods. The first antibody sequence and the reference antibody sequences should all be from a single animal, i.e., an individual mouse or an individual rabbit. In certain cases, the sequences may be aligned by eye, or by employing an alignment program such as one of the CLUSTAL suite of programs (Thompson et al Nucleic Acids Research, 22:4673-4680).

As would be apparent, the sequencing may be done using a next generation sequencing platform, e.g., Illumina's reversible terminator method, Roche's pyrosequencing method (454), Life Technologies' sequencing by ligation (the SOLiD platform) or Life Technologies' Ion Torrent platform, etc. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. In other embodiments, the sequencing may be done using nanopore sequencing (e.g. as described in Soni et al Clin Chem 53: 1996-2001 2007, or as described by Oxford Nanopore Technologies).

Depending how many sequences are obtained, this analysis may result in a list of at least 5 heavy chain sequences (e.g., at least 10, at least 50, at least 100, at least 1000 or at least 5,000 or more heavy chain sequences) that are related by lineage to the heavy chain of the first antibody, and a list of at least 5 light chain sequences (e.g., at least 10, at least 50, at least 100, at least 1000 or at least 5,000 or more light chain sequences) that are related by lineage to the light chain of the first antibody.

After the related heavy and light chain sequences have been identified, the method may comprise testing at least one of the identified heavy and light chain sequences to identify a second antibody that binds to the same antigen as the first antibody. This step may involve pairing an identified heavy chain with an identified light chain, pairing the heavy chain of the first antibody with an identified heavy chain, or pairing the light chain of the first antibody with an identified light chain. In some cases, the heavy and light chains may be combined with each other, e.g., systematically or at random, to provide antibodies that are not produced by the immunized animal, i.e., to provide a library of antibodies that contains antibodies that are neither the "first" antibody or an antibody related to the first antibody by lineage. Because the first antibody and related antibodies are related by lineage and contain minimal sequence differences relative to one another, the resultant antibodies—which contain new combinations of heavy and light chains relative to the parent and related antibodies—would be expected to be functional (i.e., would be expected to bind the same antigen as the first antibody). The new antibodies can be screened using standard methods, some of which are described below, to identify an antibody with a desired activity. This antibody may contain a heavy chain from the first antibody and a light chain from a second antibody, where the first and second antibodies are different antibodies that are related by lineage. In particular embodiments, this step may comprise testing at least 10% (e.g., at least 20%, at least 30% or at least 50%) of all possible combinations of identified heavy and light chains for binding to the antigen.

Depending on how the sequencing is done, the sequences encoding the antibodies may be made synthetically, or they may be amplified by PCR from a cDNA sample made from the animal. In either case, sequences encoding heavy and light chains may cloned into suitable vectors and expressed in a suitable host cells. Vector systems and host cells for producing antibodies are well known.

As would be readily apparent, the pairing of the heavy and light chains may be done many different ways, e.g., systematically or randomly and, in certain cases, may be done using pooled nucleic acid. In particular embodiments, the pairing may involve systematically combining the variable domains of the heavy and light chains of the first antibody and the further antibodies to produce a library of antibodies that contains at least 50% of all possible combinations of variable domains. In other embodiments, the pairing step may involve: i. introducing: a) a pool of heavy chain-encoding nucleic acid that encodes a plurality of different amplified heavy chain variable domains and b) a pool of light chain-encoding nucleic acid that encodes a plurality of different amplified light chain variable domains, into population of cells, and ii. selecting cells that contain both a heavy chain-encoding nucleic acid and a light chain-encoding nucleic acid, to produce a library of cells that produce a library of antibodies. As would be apparent, a number of different cloning strategies may be employed to produce pools of nucleic acids.

In some embodiments, the heavy and light chains can be paired and tested in a combinatorial manner using phage display methods (see, generally, Smith et al Chem. Rev. 1997 97: 391-410). In these embodiments, the heavy and light chains may be cloned into a phage display vector such that the resultant phage display library contains at least 90% of the possible combinations of heavy and light chains. The new antibodies can then be produced and tested using phage display methods, methods for which are known.

In particular embodiments, the second antibody may contain naturally paired heavy and light chain variable domains, or non-naturally paired heavy and light chain variable domains (i.e., heavy and light chain variable domains from different antibodies of the same lineage group). Since the antibodies are from the same lineage group, it is expected that such antibodies will be functional. In particular embodiments, the pairing of the heavy and light chains may be systematic (e.g., every heavy chain is tested in combination with every light chain) or random (e.g., every heavy chain is tested with randomly selected light chains), for example.

In some embodiments, the method may comprise testing the second antibody to determine the specificity or affinity to the antigen. A second antibody may inhibit at least one activity of its target in the range of about 20% to 100%, e.g., by at least about 20%, at least about 30%, at least about 40%, at least about 50%, at least about 60%, usually up to about 70%, up to about 80%, up to about 90% or more. In certain assays, a subject antibody may inhibit its target with an $IC_{50}$ of $1\times10^{-7}$M or less (e.g., $1\times10^{-7}$M or less, $1\times10^{-8}$M or less, $1\times10^{-9}$M or less, usually to $1\times10^{-12}$ M or $1\times10^{-13}$M). In assays in which a mouse is employed, a subject antibody may have an $ED_{50}$ of less than 1 µg/mouse (e.g., 10 ng/mouse to about 1 µg/mouse). In certain embodiments, a subject antibody may be contacted with a cell in the presence of a ligand, and a ligand response phenotype of the cell is monitored. The method may comprise humanizing the second antibody, methods for performing which are known.

Methods for Producing Antibodies

In many embodiments, the nucleic acids encoding a subject monoclonal antibody are introduced directly into a host cell, and the cell incubated under conditions sufficient to induce expression of the encoded antibody.

Any cell suitable for expression of expression cassettes may be used as a host cell. For example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N. Y. Acad. Sci 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In most embodiments, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule may be engineered.

Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Determining Binding Affinity of an Antibody

Once a modified antibody is produced, it may be tested for affinity using any known method, such as: 1) competitive binding analysis using a labeled (radiolabeled or fluorescent labeled) parent antibody, a modified antibody and an antigen recognized by the parent antibody; 2) surface plasmon resonance using e.g. BIACore instrumentation to provide the binding characteristics of an antibody. Using this method antigens are immobilized on solid phase chips and the binding of antibodies in liquid phase are measured in a real-time manner; 3) flow cytometry, for example, by using fluorescent activated cell sorting (FACS) analysis to study antibody binding to cell surface antigens; 4) ELISA; or 5) equilibrium dialysis. Methods for measuring binding affinity are generally described in Harlow et al., *Antibodies: A Laboratory Manual*, First Edition (1988) Cold Spring Harbor, N.Y.; Ausubel, et al, *Short Protocols in Molecular Biology,* 3rd ed., Wiley & Sons, 1995).

If affinity analysis reveals a decrease in antibody binding for the modified antibody as compared to its parent antibody, "fine tuning" may be performed to increase the affinity. One method of doing this is to systematically change back each modified residue by site-directed mutagenesis. By expressing and analyzing these back mutant antibodies, one would predict the key residues that cannot be modified without decreasing affinity.

Utility

An antibody produced by the present method finds use in diagnostics, in antibody imaging, and in treating diseases treatable by monoclonal antibody-based therapy. In particular, an antibody produced by the method described above may be humanized and used for passive immunization or the removal of unwanted cells or antigens, such as by complement mediated lysis or antibody mediated cytotoxicity (ADCC), all without substantial immune reactions (e.g., anaphylactic shock) associated with many prior antibodies. For example, the antibodies of the present invention may be used as a treatment for a disease where the surface of an unwanted cell specifically expresses a protein recognized by the antibody (e.g. HER2, or any other cancer specific marker) or the antibodies may be used to neutralize an undesirable toxin, irritant or pathogen. Humanized antibodies are particularly useful for the treatment of many types of cancer, for example colon cancer, lung cancer, breast cancer prostate cancer, etc., where the cancers are associated with expression of a particular cellular marker. Since most, if not all, disease-related cells and pathogens have molecular markers that are potential targets for antibodies, many diseases are potential indications for humanized antibodies. These include autoimmune diseases where a particular type of immune cells attack self-antigens, such as insulin-dependent diabetes mellitus, systemic lupus erythematosus, pernicious anemia, allergy and rheumatoid arthritis; transplantation related immune activation, such as graft rejection and graft-vs-host disease; other immune system diseases such as septic shock; infectious diseases, such as viral infection or bacteria infection; cardiovascular diseases such as thrombosis and neurological diseases such as Alzheimer's disease. An antibody of particular interest is one that modulates, i.e., reduces or increases a symptom of diseases such as septic shock; infectious diseases, such as viral infection or bacteria infection; cardiovascular diseases such as thrombosis and neurological diseases such as Alzheimer's disease.

An antibody of particular interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Monoclonal antibodies that have therapeutic value that have been identified using the methods and compositions of the invention are termed "therapeutic" antibodies.

Kits

Also provided by the subject invention are kits for practicing the subject methods, as described above. The subject kits at least include one or more of: an antibody made according to the above methods, a nucleic acid encoding the same, or a cell containing the same. The antibody may be humanized. Other optional components of the kit include: restriction enzymes, control primers and plasmids; buffers; etc. The nucleic acids of the kit may also have restrictions sites, multiple cloning sites, primer sites, etc to facilitate their ligation to non-rabbit antibody CDR encoding nucleic acids. The various components of the kit may be present in separate containers or certain compatible components may be precombined into a single container, as desired. In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention is are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing rabbit antibodies that are less immunogenic in a non-rabbit host than a parent antibody, or nucleotide sequences them.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of screening, comprising:
   a) obtaining the nucleotide sequences of: i. a VH cDNA, wherein said VH cDNA encodes the variable domain of a heavy chain of a first antibody of an animal; and ii. a VL cDNA, wherein said VL cDNA encodes the variable domain of a light chain of said first antibody;
   b) obtaining at least a million nucleotide sequences of cDNAs encoding at least a portion of the antibody repertoire of said animal;
   c) computationally screening the sequences obtained in b) to identify heavy and light chain sequences that are related by lineage to the heavy and light chain sequences of a); and
   d) testing in vitro at least one pair of the heavy and light chain sequences identified in c) to identify a second antibody that binds to the same antigen as the first antibody.

2. The method of claim 1, wherein the testing step d) comprises testing at least 10% of all possible combinations of heavy and light chains identified in step c) for binding to said antigen.

3. The method of claim 1, wherein the heavy and light chain sequences tested in step d) are randomly selected from the heavy and light chain sequences identified in step b).

4. A method of producing an antibody, the method comprising
   a) obtaining the nucleotide sequences of: i. a heavy chain-encoding nucleic acid that encodes the variable domain of a heavy chain of a first antibody of an animal; and ii. a light chain-encoding nucleic acid that encodes the variable domain of a light chain of the first antibody;
   b) obtaining at least a million nucleotide sequences of cDNAs encoding at least a portion of the antibody repertoire of the animal;
   c) computationally screening the sequences obtained in b) to identify heavy and light chain sequences that are related by lineage to the heavy and light chain sequences of a);
   d) introducing at least one pair of the heavy and light chain sequences obtained in c) into a host cell in vitro;
   e) incubating the host cell to permit expression of the antibody;
   f) purifying the antibody expressed in e) to produce a second antibody that binds to the same antigen as the first antibody.

5. The method according to claim 1, wherein the obtaining step b) comprises sequencing cDNAs encoding heavy and light chains made from splenocytes of said animal or from circulating B cells of said animal.

6. The method according to claim 1, wherein the obtaining step b) comprises amplifying a population of nucleic acids that encode heavy and light chains by PCR from cDNA made from antibody producing cells of said animal, and then sequencing said population of nucleic acids.

7. The method of claim 6, wherein said antibody-producing cells are not pre-selected by their ability to produce an antibody to said antigen.

8. The method according to claim 1, wherein said animal has been immunized with said antigen, multiple times, in the presence of an adjuvant.

9. The method according to claim 1, wherein said animal has an autoimmune disease, or has resistance to or has recovered from a disease.

10. The method of claim 1, wherein step b) comprises obtaining nucleotide sequences encoding at least 10% of the antibody repertoire of said animal.

11. The method of claim 1, wherein said computationally screening step c) is by comparing a sequence of at least 50 contiguous amino acids of said heavy and light chains with the sequences obtained in b).

12. The method of according to claim 1, wherein said computationally screening step c) comprises scanning the sequences obtained in step b) to identify those that encode the heavy and light chain CDR3 sequences of said first antibody.

13. The method of claim 1, comprising testing said second antibody to determine the specificity or affinity to said antigen.

14. The method of claim 1, wherein said animal is a rabbit, human, mouse or chicken.

15. The method of claim 1, further comprising humanizing said second antibody.

* * * * *